United States Patent [19]

Ichikawa et al.

[11] Patent Number: 4,774,179

[45] Date of Patent: Sep. 27, 1988

[54] PROCESS FOR PREPARING A 7-AMINOCEPHALOSPORANIC ACID COMPOUND

[75] Inventors: Shigeaki Ichikawa; Keizou Yamamoto; Kenji Matsuyama, all of Nobeoka, Japan

[73] Assignee: Asahi Kasei Kogyo Kabushiki Kaisha, Osaka, Japan

[21] Appl. No.: 753,008

[22] Filed: Jul. 9, 1985

[30] Foreign Application Priority Data

Jul. 10, 1984 [JP] Japan ................. 59-141475

[51] Int. Cl.$^4$ .............. C12P 35/02; C12N 9/80; C12R 1/38

[52] U.S. Cl. ..................... 435/51; 435/228; 435/874

[58] Field of Search ............... 435/49, 50, 51, 874, 435/196, 228

[56] References Cited

U.S. PATENT DOCUMENTS

| | | | |
|---|---|---|---|
| 3,239,394 | 3/1966 | Walton et al. | 195/36 |
| 3,945,888 | 3/1976 | Takahashi et al. | 435/50 |
| 3,960,662 | 6/1976 | Matsuda et al. | 435/51 |
| 4,141,790 | 2/1979 | Niwa et al. | 435/51 |

OTHER PUBLICATIONS

Agric. Biol. Chem., 45(7), 1561–1567, 1981.
Edwin H. Flynn: "Cephalosporins and Penicillins", pp. 37–39, Academ ic Press, New York and London, 1972.
Edwin H. Lennette et al: "Manual of Clinical Microbiology", 3rd Edition, American Soc. for Microbiology, Wash., D.C., 1980.
Noel R. Krieg et al: "Bergey's Manual of Systematic Bacteriology", vol. 1, Williams & Wilkins, Baltimore/London.

*Primary Examiner*—Elizabeth Weimar
*Attorney, Agent, or Firm*—Armstrong, Nikaido, Marmelstein & Kubovcik

[57] ABSTRACT

A process for preparing a 7-aminocephalosporanic acid compound which comprises treating a cephalosporin C compound with an enzyme-producing microorganism belonging to the genus Pseudomonas or a material obtained by subjecting the microorganism to chemical and/or physical treatment. A direct hydrolysis of the cephalosporin C compound into the 7-aminocephalosporanic acid compound and D-α-aminoadipic acid can be attained by the microorganism or material.

3 Claims, No Drawings

PROCESS FOR PREPARING A 7-AMINOCEPHALOSPORANIC ACID COMPOUND

This invention relates to a process for preparing a 7-aminocephalosporanic acid compound. More particularly, this invention is concerned with enzymatic preparation of a 7-aminocephalosporanic acid compound using a specific strain of a microorganism belonging to the genus Pseudomonas.

Various methods are known in the art to obtain a 7-aminocephalosporanic acid compound from a cephalosporin C compound by removing an acyl group bonded to the C-7 amino group in the 7-position of the latter compound produced through a fermentation process. The 7-aminocephalosporanic acid compound is useful as a starting material for cephalosporin antibiotics which are a valuable medicine.

The methods for removing the N-acyl group from a cephalosporin C compound may be classified into three types, i.e. (1) a customary chemical process, (2) an enzymatic process in which a 7β-(4-carboxybutanamido)-cephalosporanic acid compound is prepared as an intermediate and (3) an enzymatic process in which the N-acyl group is directly removed from a cephalosporin C compound. Among these processes, the customary chemical process is disadvantageous from the industrial viewpoint, particularly due to the necessity of multiple reaction steps using expensive reagents and to the formation of a large volume of by-products. With respect to the customary chemical process, reference may be made to, for example, Japanese Patent Application Publication Nos. 41-13862/1966 and 45-40899/1970.

In the above-mentioned enzymatic process in which a 7β-(4-carboxybutanamido)cephalosporanic acid compound is prepared as an intermediate, first, a cephalosporin C compound is converted to a 7β-(5-carboxy-5-oxopentanamido)cephalosporanic acid compound through a chemical deamination reaction in which the cephalosporin C compound is reacted with glyoxylic acid (see, for example, Japanese Patent Application Publication No. 55-12910/1980) or through a deamination reaction using an enzyme produced by a microorganism (see, for example, Japanese Patent Application Publication No. 50-7158/1975). Subsequently, the 7β-(5-carboxy-5-oxopentanamido)cephalosporanic acid compound is converted to a 7β-(4-carboxybutanamido)-cephalosporanic acid compound through a decarbonation reaction in which the former is reacted with hydrogen peroxide. Then, the 7β-(4-carboxybutanamido)-cephalosporanic acid compound is hydrolyzed into a 7-aminocephalosporanic acid compound and glutaric acid by the use of an enzyme produced by a microorganism belonging to the genus Pseudomonas [see, for example, Agriculture and Biological Chemistry, 45, 1561 (1981)]. This process is more advantageous than the aforementioned customary chemical process. However, it still has a drawback that the process must undergo three reaction steps.

The other enzymatic process is preferred in which the N-acyl group is directly removed from a cephalosporin C compound. There are publications in which a process for preparing a 7-aminocephalosporanic acid compound from a cephalosporin C compound by treating the latter with a microorganism or a material obtained by subjecting the microorganism to chemical and/or physical treatment is disclosed. In U.S. Pat. No. 3,239,394, there is disclosed a process for producing 7-aminocephalosporanic acid which comprises intimately contacting a cephalosporin from the group consisting of cephalosporin C and salts thereof in an aqueous medium with enzymes produced by a cephalosporn amidase-producing strain of a microorganism selected from the genera consisting of Brevibacterium, Archomobacterium and Flavobacterium. It is however generally known, as indicated on page 37 of Flynn, E. H. "Cephalosporins and Penicillins." Academic Press, New York, 1972, that the invention of the patent is not workable. Among other publications, there are Japanese Patent Application Laid-open Specification No. 52-143289/1977 in which a microoganism belonging to the genus Alternaria or Aspergillus is employed; Japanese Patent Application Laid-open Specification No. 53-94093/1978 in which strain BN-188 close to *Pseudomonas putida* is employed; and Japanese Patent Application Laid-open Specification No. 59-44392/1984 in which a microorganism belonging to the genus Paecilomyces is employed. These Japanese publications describe preparation of a 7-aminocephalosporanic acid compound from a cephalosporin C compound using a microorganism or a crude mixture of an enzyme. None of these publications, however, teach or suggest a direct conversion of a cephalosporin C compound to a 7-aminocephalosporanic acid compound and D-α-aminoadipic acid. Moreover, in these publications, there is no description with respect to the purification or partial purification of an enzyme capable of catalyzing preparation of a 7-aminocephalosporanic acid compound. Hence, it is not apparent whether the prior art processes are comprised of a one-step enzyme reaction catalyzed by a single enzyme. Therefore, the inventors have made extensive and intensive studies to find and isolate from the natural world a microorganism and enzyme capable of effecting a direct hydrolysis of a cephalosporin C compound into a 7-aminocephalosporanic acid compound and D-α-aminoadipic acid.

As a result, it has unexpectedly been found that the direct hydrolysis of a cephalosporin C compound into a 7-aminocephalosporanic acid compound and a D-α-aminoadipic acid can be attained by strains of a microorganism belonging to the genus Pseudomonas, which have been isolated from a soil. Based on this finding, the present invention has been completed.

It is, therefore, an object of the present invention to provide a novel enzymatic process for preparation of a 7-aminocephalosporanic acid compound by a direct hydrolysis of a cephalosporin C compound. The foregoing and other objects, features and advantages of the present invention will be apparent to those skilled in the art from the following detailed description and appended claims.

According to the present invention, there is provided a process for preparing a 7-aminocephalosporanic acid compound of the formula:

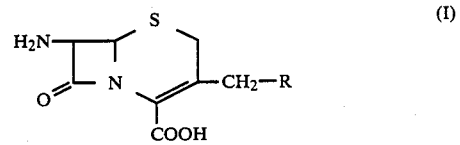

(I)

wherein R represents —OCOCH$_3$, —H or —OH, which comprises treating in an aqueous medium a cephalosporin C compound of the formula:

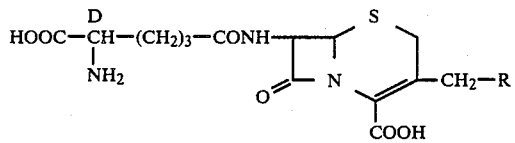

wherein R is as defined above, or a salt thereof with an enzyme-producing microorganism belonging to the genus Pseudomonas, said enzyme being capable of hydrolyzing the compound of formula (II) into the compound of formula (I) and D-α-aminoadipic acid, or with a material obtained by subjecting the microorganism to chemical and/or physical treatment.

In the present invention, a microorganism producing an enzyme capable of hydrolyzing a cephalosporin C compound into a 7-aminocephalosporanic acid compound and D-α-aminoadipic acid is employed. The inventors have found that microorganism strain designated as SE-83, which was isolated from a soil in Hokkaido, Japan and microorganism strain designated as SE-495, which was isolated from a soil in Yamaguchi, Japan are useful as such an enzyme-producing microorganism. The microorganism strains SE-83 and SE-495 have the following morphological, cultural and biochemical characteristics. With respect to the particulars of each of the test items set forth below, reference may be made to Manual of Clinical Microbiology (third edition 1980).

A. Bacteriological Properties of Strain SE-83

(I) Morphological Characteristics

Observation after culturing on a nutrient agar medium shows that the strain SE-83 is a Gram-negative rod having dimensions 0.5–0.7 μm by 1.2–1.5 μm and is motile by a polar monotrichous flagellum thereof. The microorganism does neither form a spore nor show polymorphism.

(II) Cultural Characteristics

| (1) | Culture in a nutrient agar medium | Color of growing colonies is yellowish white. Production of a diffusible pigment is not observed. The cells are not viscous and do not migrate. |
|---|---|---|
| (2) | Culture in a nutrient broth medium | The medium becomes slightly turbid. Formation of a pellicle is not observed. |
| (3) | Stab culture in a gelatin culture medium | No gelatin liquefaction is observed (25–30° C., 7 days). |
| (4) | Culture in a litmus milk medium | No casein liquefaction is observed. |

(III) Biochemical Characteristics

| (1) | Reduction of nitrate | negative. |
|---|---|---|
| (2) | Denitrification | negative. |
| (3) | MR test | negative. |
| (4) | VP test | positive. |
| (5) | Formation of indole | negative. |
| (6) | Formation of hydrogen sulfide | positive. |
| (7) | Hydrolysis of starch | negative. |
| (8) | Assimilation of citric acid | positive. |
| (9) | Assimilation of inorganic nitrogen sources | Ammonium salts are utilized as a sole nitrogen source. |
| (10) | Formation of pigment | none. |
| (11) | Oxidase | positive. |
| (12) | Catalase | positive. |
| (13) | Temperature for growth | The microorganism grows well at 25–30° C., but does not grow at 37° C. or more. |
| (14) | Behavior under aerobic or anaerobic condition | The microorganism does not grow under anaerobic condition. |
| (15) | OF test (Hugh-Leifson's method) | No acid production is observed regardless of the presence of liquid paraffin. |
| (16) | Assimilation of carbon sources | |
| | (i) Carbon sources which are utilized | malic acid, citric acid, succinic acid, glutamic acid and aspartic acid. |
| | (ii) Carbon sources which are not utilized | glucose, arabinose, xylose, mannose, galactose, fructose, maltose, sucrose, trehalose, sorbitol, mannitol, inositol, glycercol and starch. |
| (17) | Auxotrophy | The microorganism requires pantothenic acid, nicotinamide and biotin for its growth. |
| (18) | Degradation of arginine | negative. |
| (19) | Decarboxylation of lysine | negative. |
| (20) | Decarboxylation of ornithine | negative. |
| (21) | Degradation of esculin | negative. |

B. Bacteriological Properties of Strain SE-495

(I) Morphological Characteristics

Observation after culturing on a nutrient agar medium 10 shows that the strain SE-495 is a Gram-negative rod having dimensions 0.5–0.7 μm by 1.2–1.5 μm and is motile by a polar monotrichous flagellum thereof. The microorganism does neither form a spore nor show polymorphism.

(II) Cultural Characteristics

| (1) | Culture in a nutrient agar medium | Color of growing colonies is yellowish white. Production of a diffusible pigment is not observed. The cells are not viscous and do not migrate. |
|---|---|---|
| (2) | Culture in a nutrient broth medium | The medium becomes slightly turbid. Formation of a pellicle is not observed. |
| (3) | Stab culture in a gelatin culture medium | No gelatin liquefaction is observed (25° C., 14 days). |
| (4) | Culture in a litmus milk medium | No casein liquefaction is observed. |

(III) Biochemical Characteristics

| (1) | Reduction of nitrate | positive. |
|---|---|---|
| (2) | Denitrification | negative. |
| (3) | MR test | negative. |
| (4) | VP test | positive. |
| (5) | Formation of indole | negative. |
| (6) | Formation of hydrogen sulfide | negative. |
| (7) | Hydrolysis of starch | negative. |
| (8) | Assimilation of | negative. |

| | -continued | |
|---|---|---|
| | citric acid | |
| (9) | Assimilation of inorganic nitrogen sources | Ammonium salts are utilized as a sole nitrogen source. |
| (10) | Formation of pigment | none. |
| (11) | Oxidase | positive. |
| (12) | Catalase | positive. |
| (13) | Temperature for growth | The microorganism grows well at 25-30° C., but does not grow at 37° C. or more. |
| (14) | Behavior under aerobic or anaerobic condition | The microorganism does not grow under anaerobic condition. |
| (15) | OF test (Hugh-Leifson's method) | No acid production is observed regardless of the presence of liquid paraffin. |
| (16) | Assimilation of carbon sources: | |
| | (i) Carbon sources which are utilized | glutamic acid and aspartic acid. |
| | (ii) Carbon sources which are not utilized | glucose, arabinose, xylose, mannose, galactose, maltose, sucrose, sorbitol, mannitol, inositol and glycerol. |
| (17) | Auxotrophy | The microorganism requires pantothenic acid for its growth. |
| (18) | Degradation of arginine | negative. |
| (19) | Decarboxylation of lysine | negative. |
| (20) | Decarboxylation of ornithine | negative. |
| (21) | Degradation of esculin | negative. |

It is noted as a result of comparisons of the foregoing bacteriological properties to the descriptions in Bergey's Manual of Systematic Bacteriology (1984), Bergey's Manual of Determinative Bacteriology (eighth edition 1974) and Manual of Clinical Microbiology (third edition 1980) that the strains SE-83 and SE-495 are morphologically characterized by being a gram-negative rod, production of no spore and polar-monotrichate moving. Further, they are absolutely aerobic and glucose-nonfermenting bacteria. Therefore, it is concluded that the strains SE-83 and SE-495 belong to the genus Pseudomonas. Moreover, since the strains are glucose-nonoxidizers and are oxidase positive, they belong to the species close to *Pseudomonas acidovorans, Pseudomonas alcaligenes, Pseudomonas pseudoal caligenes, Pseudomonas testosteroni, Pseudomonas diminuta* or *Pseudomonas vesicularis*. It is known that of the genus Pseudomonas, the species which require growth factors are *Pseudomonas maltophilia, Pseudomonas diminuta* or *Pseudomonas vesicularis*. Hence, it is seen that the strains SE-83 and SE-495 belong to the species close to *Pseudomonas diminuta* or *Pseudomonas vesicularis*. Next, the strains SE-83 and SE-495 are negative with respect to the esculin hydrolysis test and starch hydrolysis test which are useful for distinguishing *Pseudomonas diminuta* from *Pseudomonas vesicularis*, and hence exhibit the characteristics of the species *Pseudomonas diminuta*. However, the strain SE-83 is distinct from the typical strains of *Pseudomonas diminuta* in respect of assimilation of citric acid. That is, the strain SE-83 utilizes citric acid whereas the typical strains of *Pseudomonas diminuta* do not utilize citric acid as described in Journal of General Microbiology, vol. 53, p 349 (1968). Accordingly, the inventors conclude that the strain SE-495 belongs to *Pseudomonas diminuta*, and that the strain SE-83 belongs to a novel species close to but different from *Pseudomonas diminuta*.

As described above, the microorganisms to be employed in the present invention belong to *Pseudomonas diminuta* or a species close thereto. On the other hand, according to the description on page 161 of Bergey's Manual of Systematic Bacteriology, the species of the genus Pseudomonas are classified into five groups i.e. RNA groups I, II, III, IV and V on the basis of RNA similarity. The RNA group IV includes *Pseudomonas diminuta* and *Pseudomonas vesicularis*. It is known that the bacteriological characteristics of the RNA group IV are markedly different from those of the other RNA groups. Hence, the inventors conclude that the microorganisms to be employed in the present invention are a known or novel species belonging to the RNA group IV of the genus Pseudomonas.

The microorganism strains Pseudomonas sp. SE-83 and SE-495 to be employed in the present invention have been deposited with the Fermentation Research Institute of the Agency of Industrial Science and Technology located in Ibaraki, Japan, and have been assigned Accession no. FERM BP-817 and FERM BP-818, respectively.

From a cephalosporin C compound are formed a 7-amino-cephalosporanic acid compound, a 7$\beta$-(5-carboxy-5-oxopentanamido) cephalosporanic acid compound and a 7$\beta$-(4-carboxybutanamido) cephalosporanic acid compound through an enzymatic reaction by the microorganism to be employed in the present invention. Any of the strains of the microorganism to be employed in the present invention produce a dehydrogenase by which a cephalosporin C compound is converted to a 7$\beta$-(5-carboxy-5-oxopentanamido)cephalosporanic acid compound, and two acylases by which a 7$\beta$-(4-carboxybutanamido)-cephalosporanic acid compound is hydrolyzed into a 7-aminocephalosporanic acid compound and glutaric acid. Two acylases of the strain SE-83 are designated "acylase I" and "acylase II", and two acylases of the strain SE-495 are designated "acylase I" and "acylase I(2)". Moreover, the acylase II and the acylase I(2) hydrolyze the cephalosporin C compound into a 7-aminocephalosporanic acid compound and D-$\alpha$-aminoadipic acid. The acylase II and the acylase I(2) are hereinafter collectively referred to as "cpc acylase". The cpc acylase can be released from the microorganism by ultrasonic disruption. Isolation of the cpc acylase may be effected, for example, as follows. First, the solution containing the cpc acylase is subjected to ammonium sulfate fractionation, in which the cpc acylase is precipitated at a concentration equal to 60% of the saturation concentration of ammonium sulfate. Then, the precipitated cpc acylase is dissolved in 0.1M phosphate buffer (pH 8.0) and dialyzed against the same buffer. Third, the resulting cpc acylase solution is passed through a column packed with DEAE Sephadex A-50 (manufactured and sold by Pharmacia Fine Chemicals AB, Sweden) which had been pre-equilibrated with the same buffer. As a result, the cpc acylase is adsorbed to the Sephadex resin. Subsequently, the cpc acylase is eluted by the customary concentration gradient elution method in which salt concentration is successively increased. The salt concentration at which the elution of the cpc acylase occurs differs depending on the strain of the microorganism. That is, the acylase II from the strain SE-83 is eluted at a salt concentration of from about 0.15 to about 0.2M, while the acylase I(2) from the strain SE- 495 is eluted at a salt concentration of about 0.12M. This shows that the acylase II and the acylase I(2) exhibit slightly different properties. The inventors have confirmed, using the enzymes purified by means of the DEAE Sephadex column, that the acylase II and the acylase I(2) hydrolyze a cephalosporin C compound into a 7-aminocephalosporanic acid compound and D-α-aminoadipic acid which are formed in equimolar amounts. Identification and quantity determination of a 7-aminocephalosporanic acid compound may be performed by the use of a high performance liquid chromatography. On the other hand, identification and quantity determination of D-α-aminoadipic acid may be performed by the use of an amino acid analyzer. The inventors have also confirmed, on the basis of a test in which D- and L-amino acid oxidases are used, that the α-amino-adipic acid takes a D-configuration. Trials showed that the cpc acylase is effective in hydrolyzing the compounds of Formula (II), i.e. cephalosporin C, deacetylcephalosporin C and deacetoxycephalosporin C, into corresponding 7-amino-cephalosporanic acid compounds.

The microorganisms to be employed in the present invention may be cultured in accordance with the customary culture method employed in the fermentation industry. The nutritional medium is not critical and any of those which are generally used for the culture of microorganisms may be employed in the present invention. The culture medium may consist of a carbon source, a nitrogen source and inorganic salts. As the suitable carbon source, there may be mentioned, for example, various kinds of organic acids. As the suitable nitrogen source, there may be mentioned, for example, soybean flour, wheat germ, meat extract, peptone, corn steep liquor and yeast extract. As the suitable inorganic salts, there may be mentioned, for example, magnesium salts, phosphate salts and calcium salts. According to need, additives useful for growth and activation of the microorganism may be added to the culture medium. It is preferred that the microorganism be cultured according to the aerobic liquid culture method. The culture temperature may be in the range of from 25° to 32° C., and the period of culture may be in the range of from 2 to 4 days which varies depending on the other culture conditions applied.

Using the thus obtained microorganism, the process of the present invention may be carried out in the following manner. First, the microorganism may be harvested by centrifugation or the like from the culture for the use in the process of the present invention. Alternatively, since the major portion of the cpc acylase exists generally inside the cell, the microorganism may be subjected to physical treatment such as ultrasonic disruption and/or chemical treatment such as organic solvent treatment to obtain a material such as cells having an improved permeability of substrate, disrupted cells and crude or purified enzyme in the form of a suspension or solution for the use in the process of the present invention. Examples of the methods for obtaining the material have been described above. Then, the resulting microorganism or material may be employed to treat a cephalosporin C compound or a salt thereof in an aqueous medium. The cephalosporin C compound or salt thereof may be dissolved in the aqueous medium in concentrations of from about 0.5 to about 20 mg/ml. On the other hand, the microorganism or the material may be incorporated in the aqueous medium in concentrations of from about 10 to about 100 mg or more per ml.

From the viewpoint of the reaction rate, the optimum pH values of the medium may be from about 8.0 to about 9.0. However, since a higher pH value tends to promote decomposition of the substrate and reaction product, it is generally preferred that the pH value of the medium be maintained in the range of about 7.0 to about 8.0. The enzymatic reaction for preparing a 7-aminocephalosporanic acid compound may be conducted at a temperature of from about 20° to about 40° C., preferably from about 25° to about 37° C., for a period of from about 2 to about 12 hr. The above temperature is desirable from the viewpoints of the thermal stability of the enzyme and the reaction rate. The above period may be varied depending on the concentration of the substrate and other reaction conditions. In one mode of the process of the present invention, the cephalosporin C compound may be treated in a vessel such as a tank by the microorganism or the material such as cells having an improved permeability of substrate, disrupted cells and crude or purified enzyme in the form of a suspension or solution. In another mode of the process of the present invention, the treatment of the cephalosporin C compound may be effected by passing a solution thereof through a column packed with immobilized cells or immobilized enzyme. As mentioned above, if the dehydrogenase is active in the reaction system, intermediates are produced. However, it does not affect the enzymatic reaction of the cpc acylase in the process of the present invention.

Separation from the reaction mixture and purification of a 7-aminocephalosporanic acid compound of formula (I) may be effected by the customary methods such as column chromatography method and isoelectric point precipitation method. The quantitative analysis of the reaction product may be carried out as follows. With respect to 7-aminocephalosporanic acid, the quantitative analysis may be conducted in accordance with a high performance liquid chromotography method using the $\mu$-Bondapak $C_{18}$ column (manufactured and sold by Waters Associates, Massachusetts, U.S.A.) and a mobile phase of a mixture consisting of 98% by volume of 5% by weight aqueous ammonium acetate and 2% by volume of acetonitrile. The detection of the ultimate compound may be effected at 260 nm. With respect to the compound of formula (I) other than 7-aminocephalosporanic acid, it may be converted to a N-phenylacetyl derivative and then the amount of the derivative may be determined. The determination of the amount of the reaction product may be conducted, for example, as follows. First, sodium bicarbonate is added to the aqueous solution containing the desired product to render the solution alkaline. To the resulting alkaline solution are added 1/10 volume of acetone and an excess amount (about 5-fold mole against the estimated amount of the product) of phenylacetyl chloride. The mixture is maintained at room temperature to obtain a phenylacetyl derivative. Half an hour later, the unreacted phenylacetyl chloride is extracted with ½ volume of diethyl ether. The remaining aqueous phase is adjusted to pH 2, and ed to an extraction with equivolume of ethyl acetate twice. The ethyl acetate layers are collected and dried under reduced pressure. The residue is dissolved in a predetermined amount of methanol, and subjected to a high performance liquid chromatography to determine the amount of the N-phenylacetyl derivative. In the liquid chromatography, the above-mentioned $\mu$-Bondapak $C_{18}$ column is employed and a mixture of 0.05M phosphate buffer (pH 7.0) and methanol is employed as a mobile phase. The detection of the derivative is effected at 260 nm. The yield of the 7-aminocephalosporanic acid compound is calculated from the thus determined amount of the formed N-phenylacetyl derivative and the recovery rate obtained in a reference test using a known concentration of the compound.

As described above, the inventors have found and completed a novel and advantageous process for preparing a 7-aminocephalosporanic acid compound with the microorganism belonging to the genus Pseudomonas, on the basis of the findings that a group of microorganisms belonging to the genus Pseudomonas produce a group of cpc acylases which hydrolyze a cephalosporin C compound into a 7-aminocephalosporanic acid compound and D-$\alpha$-aminoadipic acid.

The present invention will be illustrated in more detail with reference to the following Examples, which should not be construed to be limiting the scope of the present invention.

EXAMPLE 1

15 liters of a culture medium (pH 7.0) comprising 0.2% by weight of meat extract, 0.2% by weight of yeast extract, 0.5% by weight of peptone, 0.5% by weight of monosodium glutamate and 0.005% by weight of magnesium sulfate were charged into a 30-liters jar fermentor. After sterilization at 120° C. for 30 minutes, 300 ml of a seed culture in which Pseudomonas sp. SE-83 had been cultivated in the same medium in advance was put in the fermentor. After incubation at 25° C. for 48 hours, the bacterial cells were harvested by centrifugation to obtain 52 g of wet cells. 10 g of the obtained wet cells were suspended in 200 ml of 0.05M phosphate buffer (pH 7.5). 2 ml of chloroform was added to the suspension and shaked at 32° C. for 30 minutes. Then, 1.4 g of cephalosporin C was added and reaction was effected at 37° C. for 4 hours. After completion of the reaction, the yield of 7-aminocephalosporanic acid in the reaction mixture was 8% (mole of product/mole of starting material x 100). The yield was determined in accordance with the high performance liquid chromatography method as described hereinbefore.

Cells were removed from the reaction mixture and the reaction mixture was diluted with water 3-fold. Then, the diluted mixture was passed through a column packed with 400 ml of DEAE Sephadex A-25 (Cl$^-$ type, manufactured and sold by Pharmacia Fine Chemicals AB, Sweden). The column was washed with about 600 ml of water and then an 0.05M aqueous NaCl solution was applied to the column to elute 7-aminocephalosporanic acid. Fractions of 7-aminocephalosporanic acid were collected and adjusted to pH 7.0 followed by contentration under reduced pressure. Then, the concentrated solution was passed through a column packed with 100 ml of Diaion HP-20 (trade name for a porous polymer manufactured and sold by Mitsubishi Chemical Industried Limited, Japan) which had been washed with 0.1M phosphate buffer (pH 7.0) in advance, and the column was sufficiently washed with deionized water followed by elution with a 50% aqueous methanol solution. Fractions of 7-aminocephalosporanic acid were collected and concentrated under reduced pressure. Then, the concentrated solution was adjusted to pH 3.0 and allowed to stand at a cool place to precipitate 7-aminocephalosporanic acid. The precipitate was collected and dried in vacuo to obtain 46 mg of 7-aminocephlosporanic acid having a purity of 80%.

EXAMPLE 2

1 g of wet cells were obtained in substantially the same manner as described in Example 1. The obtained cells were suspended in 20 ml of 0.1M phosphate buffer (pH 7.0) and subjected to ultrasonic disruption at 5° C. Then, 100 mg of cephalosporin C was added to the disrupted cell suspension and the resulting mixture was reacted at 30 ° C. for 10 hours. After completion of the reaction, the yield of 7-aminocephalosporanic acid in the mixture was 5.5%.

EXAMPLE 3

1 g of wet cells were obtained in substantially the same manner as described in Example 1. The obtained cells were suspended in 20 ml of 0.1M phosphate buffer (pH 7.5). Then, 0.5 ml of toluene was added and the resulting mixture was shaked at 5° C. for 30 minutes. 50 mg of deacetylcephalosporin C was added to the mixture and reaction was effected at 25° C. for 8 hours. After completion of the reaction, the yield of 7-aminodeacetylcephalosporanic acid was 4.5%.

EXAMPLE 4

20 g of wet cells were obtained in substantially the same manner as described in Example 1. The obtained cells were suspended in 100 ml of 0.1M phosphate buffer (pH 7.0) and subjected to ultrasonic disruption at 5° C. Then, solid materials were removed to prepare a cell-free enzyme solution. The obtained enzyme solution was subjected to ammonium sulfate fractionation. That is, ammonium sulfate was gradually added to the solution, while stirring, to a concentration equal to 30% of the saturation concentration at a temperature of 5° C. to form a precipitate and the formed precipitate was removed. To the supernatant fraction, ammonium sulfate was added to a concentration equal to 60% of the saturation concentration and stirred for 1 hour. Then, the precipitate was collected and dissolved in 50 ml of 0.1M phosphate buffer (pH 8.0). The thus obtained enzyme solution was dialyzed against the same buffer at 5° C. overnight and then passed through a column packed with DEAE Sephadex A-50 (manufactured and sold by Pharmacia Fine Chemicals AB, Sweden) which had been pre-equilibrated with the same buffer. As a result, the cpc acylase was adsorbed. The elution of the enzyme was carried out in accordance with the concentration gradient elution method in which salt concentration is successively increased. In this Example, 0.1M phosphate buffer (pH 8.0) was used as an eluate in a volume 5 times that of the column and the NaCl concentration was linearly increased to a final concentration of 0.3M. The active fractions eluted at 0.15–0.2M were collected and concentrated to a volume of 5 ml using an ultrafiltration apparatus (manufactured by Asahi Kasei Kogyo Kabushiki Kaisha). To the obtained concentrated mixture was added 30 mg of cephalosporin C and reaction was effected at 30° C. for 12 hours. The yield of 7-aminocephalosporanic acid was 10%.

EXAMPLE 5

Pseudomonas sp. SE-495 was cultured in substantially the same manner as described in Example 1 to obtain 50 g of wet cells. In substantially the same manner as described in Example 4, 20 g of the obtained cells were subjected to ultrasonic disruption, ammonium sulfate fractionation, fractionation using a column of DEAE Sephadex and concentration using the ultrafiltration apparatus. Thus, there was obtained 5 ml of a purified enzyme solution. To the obtained solution was added 30 mg of cephalosporin C and reaction was effected at 25° C. for 3 hours while adjusting the solution to pH 8.0 using an 6N aqueous NaOH solution. The yield of 7- aminocephalosporanic acid was 8%.

What is claimed is:

1. A process for preparing a 7-aminocephalosporanic acid compound of the formula:

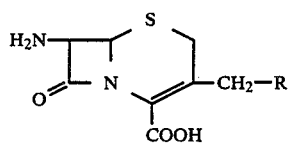

wherein R represents —OCOCH$_3$, —H or —OH, which comprises treating in an aqueous medium a cephalosporin C compound of the formula:

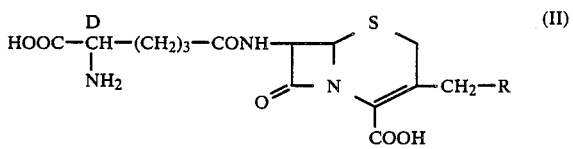

wherein R is as defined above, or a salt thereof, with a microorganism selected from the group consisting of Pseudomonas sp. SE-83 (Fermentation Research Institute Accession No. FERM BP-817) and Pseudomonas sp. SE-495 (Fermentation Research Institute Accession No. FERM BP-818), or with a material obtained by subjecting the microorganism to chemical and/or physical treatment.

2. A process according to claim 1, wherein the microorganism is Pseudomonas sp. SE-83 (Fermentation Research Institute Accession No. FERM BP-817).

3. A process according to claim 1, wherein the microorganism is Pseudomonas sp. SE-495 (Fermentation Research Institute Accession No. FERM BP-818).

* * * * *